(12) United States Patent
Helmus et al.

(10) Patent No.: US 8,221,783 B2
(45) Date of Patent: Jul. 17, 2012

(54) MEDICAL DEVICES WITH TRIGGERABLE BIOADHESIVE MATERIAL

(75) Inventors: Michael N. Helmus, Worcester, MA (US); Yixin Xu, Newton, MA (US); Barron W. Tenney, Haverhill, MA (US); Paul L. Valint, Pittsford, NY (US); Shrirang V. Ranade, Arlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 154 days.

(21) Appl. No.: 12/207,839

(22) Filed: Sep. 10, 2008

(65) Prior Publication Data

US 2009/0098176 A1    Apr. 16, 2009

Related U.S. Application Data

(60) Provisional application No. 60/971,052, filed on Sep. 10, 2007.

(51) Int. Cl.
| | |
|---|---|
| *C08B 37/08* | (2006.01) |
| *C08L 71/02* | (2006.01) |
| *A61K 47/36* | (2006.01) |
| *A61K 47/42* | (2006.01) |
| *A61K 9/70* | (2006.01) |
| *A61K 9/00* | (2006.01) |
| *A61K 31/337* | (2006.01) |
| *A61K 31/436* | (2006.01) |
| *A61K 47/38* | (2006.01) |
| *A61F 2/02* | (2006.01) |
| *C07K 14/78* | (2006.01) |
| *C08F 210/00* | (2006.01) |
| *C08G 63/06* | (2006.01) |
| *C08G 67/00* | (2006.01) |
| *C08G 73/00* | (2006.01) |
| *C08G 73/10* | (2006.01) |

(52) U.S. Cl. ........ 424/434; 424/422; 526/348; 526/258; 528/367; 536/56; 536/30; 536/58; 536/3; 536/20; 525/408; 530/354; 514/772.3; 514/772.4; 514/772.6; 514/291; 514/279; 514/449; 514/777; 514/779; 514/781; 514/773; 514/774; 623/11.11; 623/1.16; 623/1.46; 623/1.42; 623/1.36

(58) Field of Classification Search ........................ None
See application file for complete search history.

(56) References Cited

U.S. PATENT DOCUMENTS

| | | | |
|---|---|---|---|
| 4,655,771 | A | 4/1987 | Wallsten |
| 4,954,126 | A | 9/1990 | Wallsten |
| 5,061,275 | A | 10/1991 | Wallsten et al. |
| 5,269,810 | A * | 12/1993 | Hull et al. ..................... 607/129 |
| 5,449,373 | A | 9/1995 | Pinchasik et al. |
| 6,726,696 | B1 * | 4/2004 | Houser et al. ................. 606/151 |
| 6,733,788 | B2 | 5/2004 | McBride et al. |
| 6,827,727 | B2 * | 12/2004 | Stålemark et al. ............. 606/201 |
| 6,893,431 | B2 * | 5/2005 | Naimark et al. ........... 604/891.1 |
| 7,276,246 | B2 * | 10/2007 | Zhang ........................... 424/434 |
| 2003/0077253 | A1 | 4/2003 | Palasis |
| 2007/0020321 | A1 * | 1/2007 | Redding et al. ............... 424/447 |
| 2007/0083137 | A1 * | 4/2007 | Hopman et al. ................ 602/48 |
| 2007/0149496 | A1 * | 6/2007 | Tuszynski et al. ............ 514/184 |
| 2007/0208141 | A1 | 9/2007 | Shull et al. |
| 2007/0254016 | A1 * | 11/2007 | Andersen et al. ............. 424/443 |
| 2008/0215132 | A1 * | 9/2008 | Ryan et al. .................... 623/1.15 |

FOREIGN PATENT DOCUMENTS

| | | |
|---|---|---|
| DE | 10113988 A1 | 10/2001 |
| WO | 94/16646 A1 | 8/1994 |
| WO | WO 00/59558 * | 3/2000 |
| WO | 00/54832 A1 | 9/2000 |
| WO | 00/59558 A1 | 10/2000 |
| WO | 02/34304 A1 | 5/2002 |
| WO | 03/082163 A1 | 10/2003 |
| WO | 2005/058383 A2 | 6/2005 |
| WO | 2005/101045 A1 | 10/2005 |
| WO | 2006/068838 A2 | 6/2006 |
| WO | 2007/095167 A2 | 8/2007 |

* cited by examiner

*Primary Examiner* — Robert A Wax
*Assistant Examiner* — Danah Al-Awadi
(74) *Attorney, Agent, or Firm* — Mayer & Williams PC; David B. Bonham; Keum J. Park

(57) ABSTRACT

Described herein are implantable medical devices comprising a biocompatible polymer comprising a triggerable bioadhesive property that allows the device to adhere to body tissue. The triggerable bioadhesive property of the polymer can be triggered or activated by exposure to a stimulus. Also, the present invention pertains to methods of making an implantable medical device comprising a biocompatible polymer comprising a triggerable bioadhesive property that allows the device to adhere to body tissue.

33 Claims, 12 Drawing Sheets

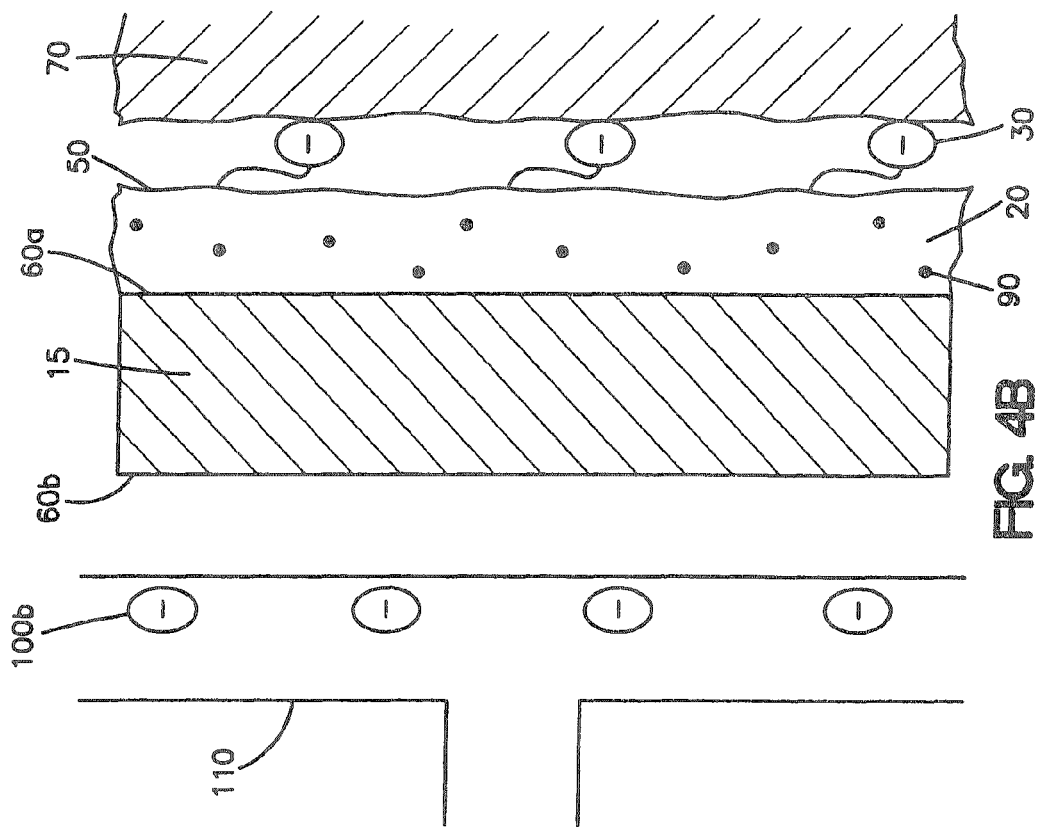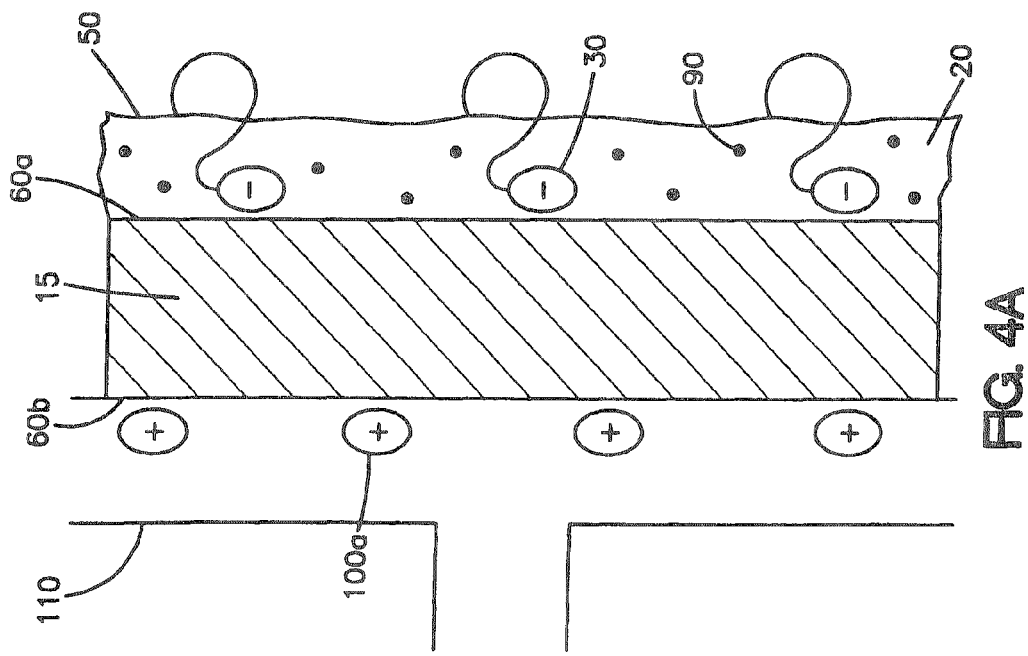

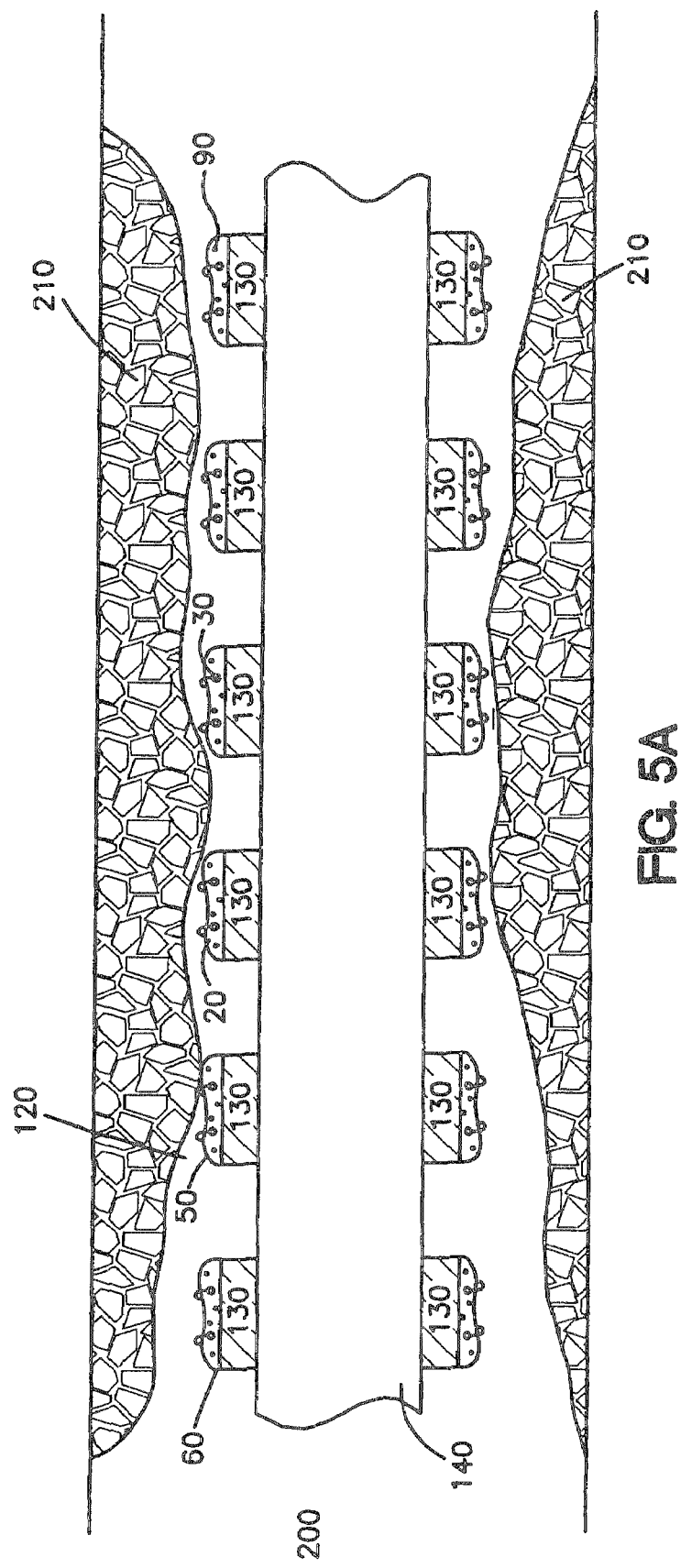

MEDICAL DEVICES WITH TRIGGERABLE BIOADHESIVE MATERIAL

STATEMENT OF RELATED APPLICATIONS

This application claims the benefit of U.S. Provisional Patent Application Ser. No. 60/971,052, filed Sep. 10, 2007, entitled "Medical Devices With Triggerable Bioadhesive Material", which is incorporated in its entirety by reference herein.

INTRODUCTION

Described herein are medical devices having a biocompatible polymer with triggerable bioadhesive properties that allow the medical device to adhere to body tissue when the triggerable bioadhesive properties are triggered by a stimulus. In some embodiments, the polymer retains its bioadhesive properties after the stimulus has been removed. In other embodiments, the polymer becomes non-bioadhesive after the stimulus has been removed. Also, described herein are methods of making implantable medical devices that include biocompatible polymers having triggerable bioadhesive properties.

BACKGROUND

In order to effectively treat a localized area of body tissue, a therapeutic agent may need to be maintained at the treatment site for an effective period of time. Problems arise, however, when therapeutic agents need to be applied to a site that is covered by or constantly exposed to body fluids. Such fluids tend to rapidly wash away the therapeutic agents. For example, when therapeutic agents are applied to the buccal cavity, saliva production and natural replacement of the mucosal tissue limit the effectiveness and residence time of therapeutic agents. Additionally, therapeutic agents introduced to a body lumen, such as an artery, can be swept downstream by blood flow.

In order to address the specific environment of certain body tissues, medical devices with bioadhesive properties have been created to treat wounds and deliver therapeutic agents to such body tissues. Bioadhesion refers to the ability of certain materials such as, polymers, macromolecules and hydrocolloids to adhere to biological or body tissue. Bioadhesion is a complex phenomenon, depending in part upon the properties of the bioadhesive materials, the treatment site and the environment surrounding the treatment site. Several factors have been found to contribute to the bioadhesive capability of polymers including the molecular weight of the polymer, the presence of functional groups and anionic charges, the strength of anionic charges and the ability of the polymer chains to interpenetrate the mucous layer.

In the past, bioadhesive materials have commonly been used in dentistry, orthopedics, ophthalmology, and in surgical applications. Recently, bioadhesive materials have been used in other areas such as soft tissue-based artificial replacements, and controlled release systems for local release of therapeutic agents to deliver therapeutic agents to the nasal cavity or intestines.

As medical procedures become more specialized, the need for bioadhesive materials that offer a high degree of control and accuracy increases. In order to better control such bioadhesive materials, the bioadhesive properties of the bioadhesive material should be able to be switched on and off as needed. Accordingly, there is a need for improved bioadhesive materials that can offer the user increased control of the bioadhesive properties and greater accuracy during the application of the system to the treatment site.

SUMMARY

These and other objectives are accomplished by the embodiments described herein. In certain embodiments, medical devices, such as a patch or a stent, include a biocompatible polymer that has triggerable bioadhesive properties. The triggerable bioadhesive properties of the polymer can be activated upon exposure to a stimulus. Once activated or "triggered" the bioadhesive properties of the polymer allow the medical device to adhere to body tissue. As used herein and unless otherwise specified the term "adhere" means to attach to or to remain in association with. For example, the bioadhesive properties of the polymers of the embodiments described herein are capable of allowing the polymer to attach to or to remain in association with a biological surface, such as a body lumen, body tissue or mucosal surface.

In certain embodiments, a medical device for implantation in the body of a patient includes a biocompatible polymer having a triggerable bioadhesive property that allows the implantable medical device to adhere to body tissue when the polymer is exposed to a stimulus.

For example, the medical devices described here include an implantable patch that has a first surface and a first coating disposed on the first surface, wherein the first coating includes a first biocompatible polymer having a first triggerable bioadhesive property that allows the patch to adhere to body tissue when the first polymer is exposed to a first stimulus. Additionally, the patch can include a second surface that is opposite the first surface and a second coating disposed on the second surface, wherein the second coating includes a second biocompatible polymer having a second triggerable bioadhesive property that allows the patch to adhere to a surface when the second polymer is exposed to a second stimulus.

In other embodiments, medical devices described herein include an intravascular stent having a balloon-expandable, tubular sidewall stent structure having a plurality of struts and a plurality of openings and a coating conforming to the stent sidewall structure so as to preserve the plurality of openings therein. The coating includes an anti-restenotic agent and a biocompatible polymer having triggerable bioadhesive properties that allow the stent to adhere to a blood vessel when the polymer is exposed to a stimulus.

BRIEF DESCRIPTION OF THE DRAWINGS

FIG. 4A shows a patch with a coating of a biocompatible polymer having triggerable bioadhesive properties disposed on a surface of the patch being delivered by a delivery device.

FIG. 4B shows the patch of FIG. 4A being released from the delivery device and adhering to body tissue.

FIG. 5A shows an intravascular stent with a coating that includes a biocompatible polymer with triggerable bioadhesive properties being delivered to an occlusion in a blood vessel.

DETAILED DESCRIPTION

Medical Devices that Include Polymers with Triggerable Bioadhesive Properties

Figure 1A:
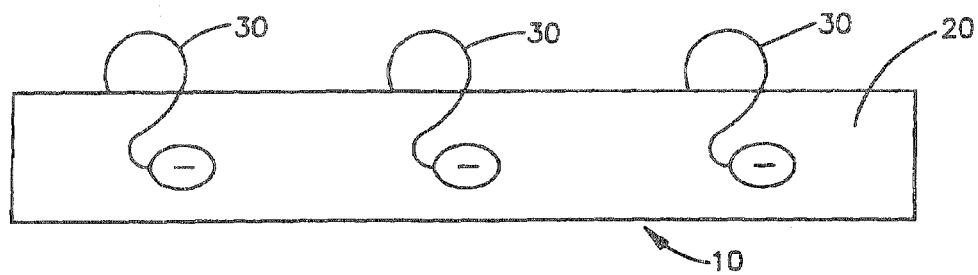
FIG. 1A shows a cross-sectional view of a medical device, such as a patch, that includes a biocompatible polymer with triggerable bioadhesive properties, wherein the polymer is in a non-bioadhesive state.

FIG. 1A shows a cross-sectional view of one embodiment described herein. As shown in FIG. 1A, medical device 10 comprises a biocompatible polymer 20 with triggerable bioadhesive properties that allow the device to adhere to body tissue when the triggerable bioadhesive properties are activated. The triggerable bioadhesive properties are activated by exposing the polymer to a stimulus. In FIG. 1A, medical device 10, comprising a biocompatible polymer 20 with triggerable bioadhesive properties, is not exposed to a stimulus, thus the bioadhesive properties are inactive and the polymer is non-bioadhesive. Polymer 20 derives its bioadhesive properties from bioadhesive functionalities 30. When the polymer 20 is exposed to a stimulus the bioadhesive functionalities 30 are activated and provide the polymer 20 with bioadhesive properties.

Bioadhesive functionalities are the properties of the polymer that enable the bioadhesiveness of the polymer to be controlled. In certain embodiments, the bioadhesive functionalities are embedded in or bonded to the polymer. Examples of bioadhesive functionalities include functional groups embedded in or bonded to the polymer. Additionally, bioadhesive functionalities include exposed oligomer groups or oligomer groups that are capable of being exposed. Generally, these bioadhesive functionalities are located at or near the surface of the device. As shown in FIG. 1A, the bioadhesive functionalities are negatively charged. However, such bioadhesive functionalities can be positively charged or have both positively and negatively charged bioadhesive functionalities, or be neutral.

Figure 1B:
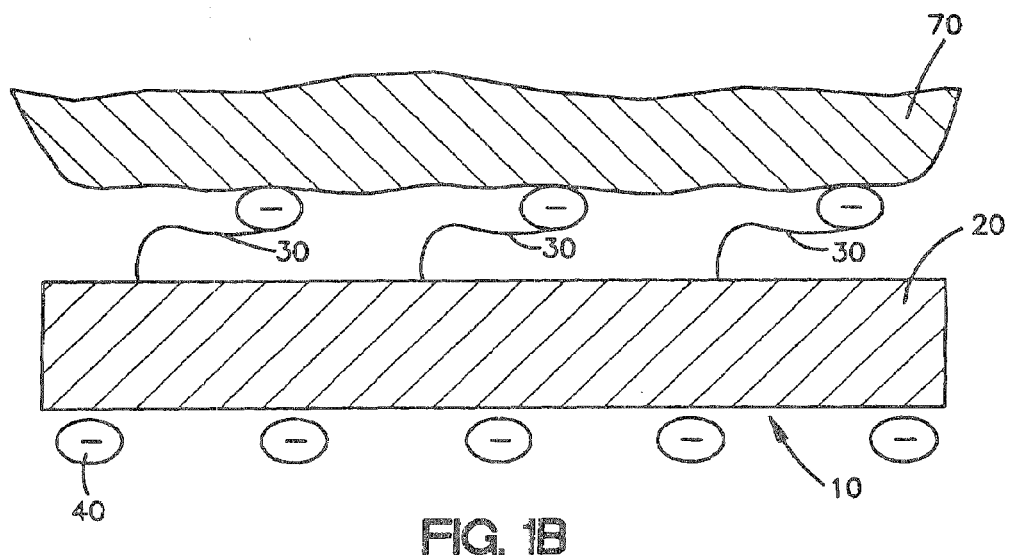
FIG. 1B shows a cross-sectional view of the device of FIG. 1A when the triggerable bioadhesive properties are activated by a stimulus, such as an electric potential.

FIG. 1B shows medical device 10 after the polymer 20 has been exposed to a stimulus, which in this embodiment is a negative electrical potential 40. Other examples of suitable stimuli are discussed below. The bioadhesive functionalities 30, which in this example are negatively charged, are activated, giving the medical device bioadhesive properties. The bioadhesive properties allow the medical device 10 to adhere to the body tissue 70. In this example, the stimulus is applied to the side of the medical device 10 that is opposite the side that will contact the body tissue. However, the stimulus can be applied directly or indirectly to other parts of the medical device.

Figure 2A:
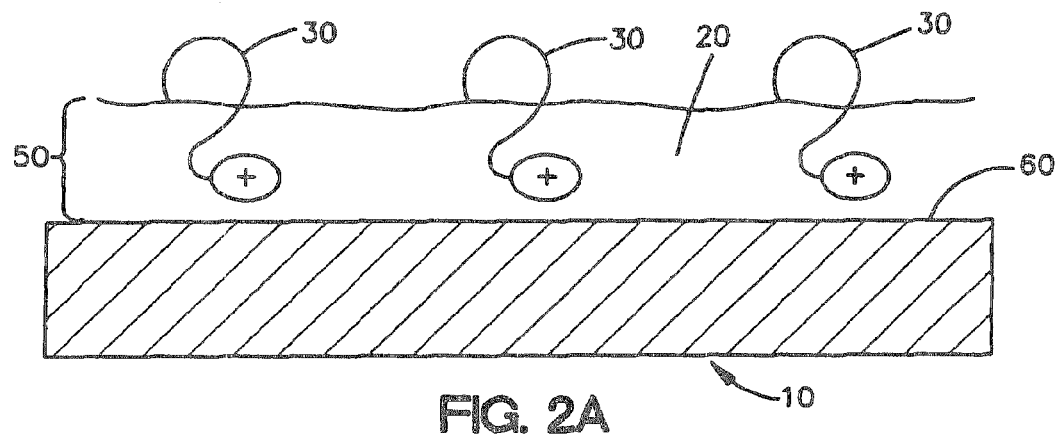
FIG. 2A shows a cross-sectional view of a patch with a coating disposed on the surface of the patch, wherein the coating includes a biocompatible polymer with triggerable bioadhesive properties.

FIG. 2A shows another embodiment where a coating 50 is disposed onto the surface 60 of a medical device 10. The coating 50 includes a biocompatible polymer 20 with triggerable bioadhesive properties. Polymer 20 has bioadhesive functionalities 30, which in this embodiment, are positively charged. As shown in FIG. 2A the medical device 10 is not exposed to a stimulus, therefore the bioadhesive properties are inactive and the polymer 20 is non-bioadhesive. The triggerable bioadhesive properties can be activated by exposing them to a positive electrical potential or another stimulus. In some embodiments, the bioadhesive properties of the polymer can be deactivated after the polymer is no longer exposed to the stimulus. In other embodiments, the polymer can remain bioadhesive even after the stimulus is removed from the polymer. In such embodiments, the activated bioadhesive properties can be deactivated by re-applying the same stimulus or by applying another type of stimulus.

Figure 2B:
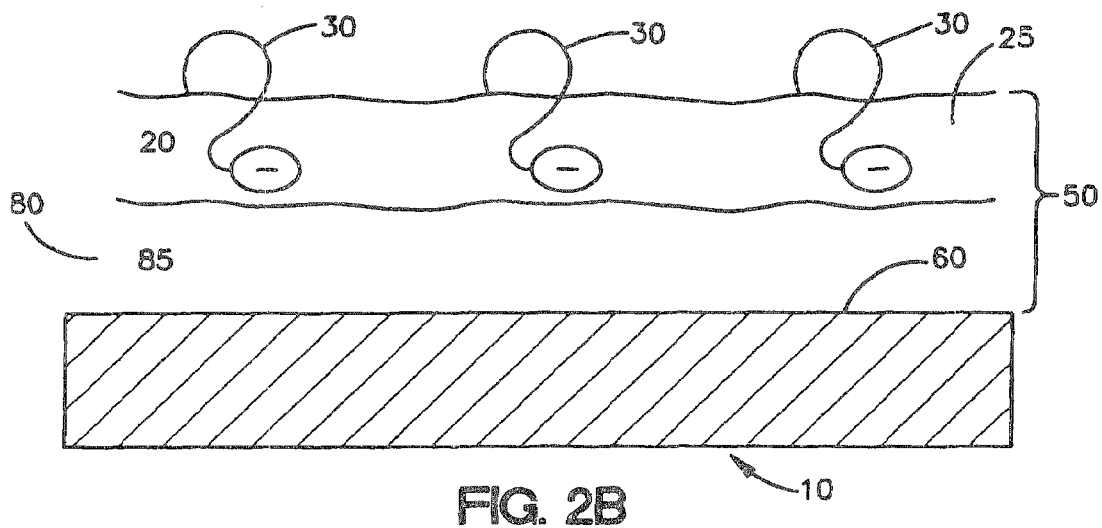
FIG. 2B shows a cross-sectional view of a patch with a coating disposed over the surface of the patch, wherein the coating includes a biocompatible polymer having a first polymer and a second polymer, wherein the second polymer has triggerable bioadhesive properties.

Biocompatible polymers having triggerable bioadhesive properties can comprise more than one type of polymer. Each different type of polymer may or may not have triggerable bioadhesive properties. In one embodiment, a first polymer can be embedded within a second polymer. For example, a biocompatible polymer having triggerable bioadhesive properties can comprise a first polymer and a second polymer, wherein the first polymer does not have triggerable bioadhesive properties and wherein the second polymer has triggerable bioadhesive properties. The second polymer can be embedded in the first polymer or vice versa. Alternatively, the first and second polymer can be formed into layers. FIG. 2B shows a medical device 10 comprising a surface 60 and a coating 50 disposed on the surface 60. The coating 50 comprises a first layer 80 comprising a polymer 85 without bioadhesive properties. The coating 50 also includes a second layer 25 comprising a polymer 20 with triggerable bioadhesive properties. The polymer 20 comprises bioadhesive functionalities 30. In alternative embodiments, the coating 50 can comprise additional layers that comprise polymers with or without triggerable bioadhesive properties. Generally, the layers can be any thickness that allow the triggerable bioadhesive properties of the polymer to be activated and deactivated. In certain embodiments, each layer can have a thickness ranging from monomolecular to tens of microns. The total thickness of the coatings described herein can range from nanometers to tens of microns. For example, the thickness of coatings can be about 1 nm to about 50 microns. Additionally, when the medical device is comprised entirely of a biocompatible polymer, such as a patch, the thickness of the biocompatible polymer can range from tens of microns to millimeters. For example, the thickness of a patch comprising a biocompatible polymer can be about 10 microns to about 5 millimeters.

Figure 2C:
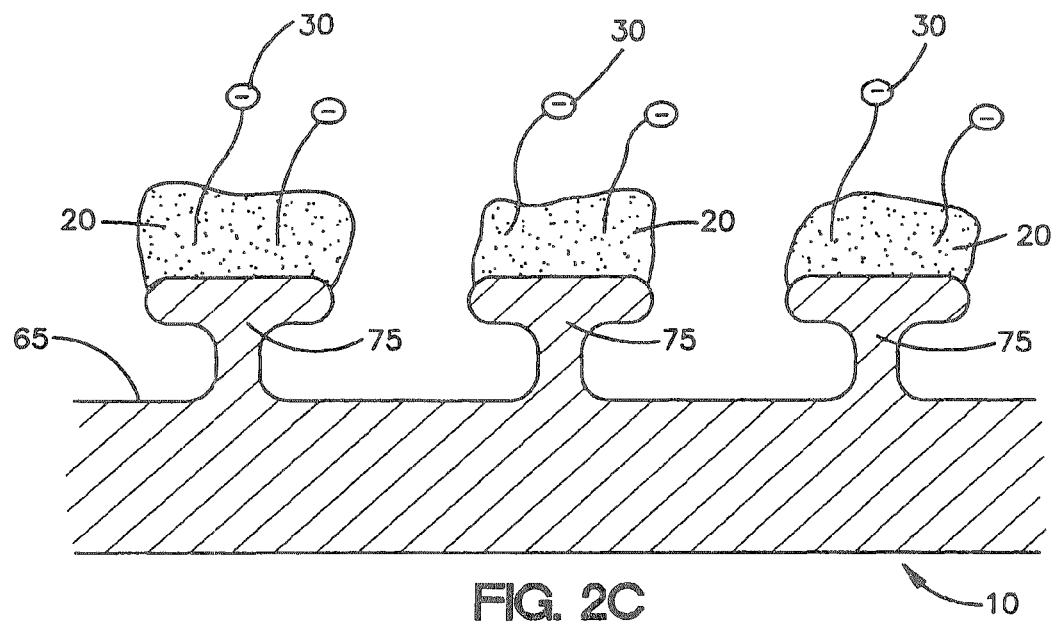
FIG. 2C shows a cross-sectional view of a medical device with a textured surface and a coating disposed on portions of the surface, wherein the coating includes a biocompatible polymer with triggerable bioadhesive properties.

Also in accordance with the embodiments described herein, the biocompatible polymer can be disposed on specific portions of a medical device. For example, when the medical device has a textured surface, the polymer having bioadhesive properties can be disposed on select portions of the textured surface. FIG. 2C shows a medical device 10 with a textured surface 65 having protrusions or "gecko-feet" 75. A biocompatible polymer 20 with bioadhesive functionalities 30 is disposed on the gecko feet 75. The use of textured surfaces in medical devices may enhance the speed and strength at which medical devices adhere and detach from body tissue or other surfaces. This increase in the speed and strength of attachment can be attributed to the increased surface area of the textured surface that allows for a greater amount of polymer to be disposed on the surface of the medical device and, therefore, a higher concentration of bioadhesive functionalities on the surface of the medical device. The polymer 20 can be applied to a portion of a textured surface by any method known in the art including, spraying, dipping, brushing, chemical vapor deposition (CVD), physical vapor deposition (PVD), lithography or similar processes.

Figure 3:
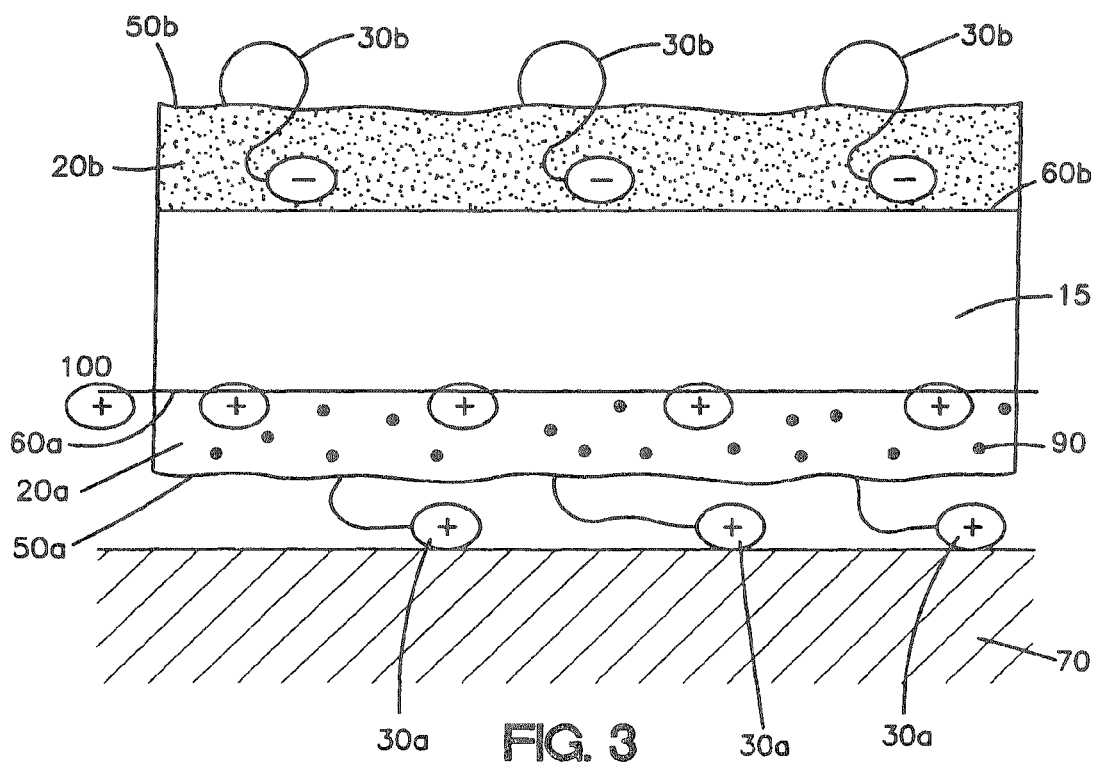
FIG. 3 shows a patch with a coating of a first biocompatible polymer with triggerable bioadhesive properties disposed on a surface of the patch and a coating of a second biocompatible polymer with triggerable bioadhesive properties disposed on the opposite surface of the patch.

FIG. 3 shows a patch 15 having a first surface 60a, the surface that faces the body tissue 70 and a second surface 60b that is opposite the first surface 60a. A first coating 50a is disposed on the first surface 60a. The first coating 50a comprises a first biocompatible polymer 20a, which has positively charged bioadhesive functionalities 30a. The first coating 50a also comprises a therapeutic agent 90. A second coating 50b is disposed on the second surface 60b. The second coating 50b comprises a second biocompatible polymer 20b, which has negatively charged bioadhesive functionalities 30b.

In this embodiment, a positive electric potential 100 has been applied to the patch 15. The positive electric potential activates the bioadhesive properties of the first polymer 20a disposed on the first surface of the patch 60a while allowing the bioadhesive properties of the second polymer 20b, disposed on the second surface of the patch 60b, to remain inactive. This allows the patch 15 to adhere to the body tissue 70. Alternatively, to remove the patch, a negative potential can be applied to the patch which will deactivate the bioadhesive properties of the first polymer 20a disposed on the first surface of the patch 60a and activate the bioadhesive properties of the second polymer 20b disposed on the second surface of the patch 60b. This will allow the patch to release from the body tissue 70 and attach to a second medical device that is capable of removing the patch.

FIG. 4A shows a patch 15 having a coating 50 disposed on surface 60a of the patch 15. The coating 50 comprises a biocompatible polymer 20 that has triggerable bioadhesive properties. The polymer 20 includes negatively charged bioadhesive functionalities 30. The coating 50 also comprises a therapeutic agent 90. The patch 15 is disposed on a delivery device 110. In this embodiment, the patch 15 is maintained on the delivery device 110 by using a positive electrical potential 100a that attracts the negatively charged bioadhesive functionalities 30 and causes the bioadhesive functionalities 30 to be inactivated. In an alternative embodiment, the coating 50 can also be applied to surface 60b.

FIG. 4B shows patch 15 of FIG. 4A adhering to body tissue 70. In this embodiment, the delivery device 110 supplies a negative electric potential 100b to patch 15. The negatively charged bioadhesive functionalities 30 of polymer 20 are activated and the patch 15 adheres to the body tissue 70. After adhesion of patch 15 to the body tissue 70, therapeutic agent 90 can be delivered.

In an alternative embodiment, a delivery device can enable a patch, or other medical device, to adhere to body tissue by applying pressure as a stimulus. For instance, the biocompatible polymer with triggerable bioadhesive properties can be pressure-sensitive such that when the delivery device applies a pressure against the patch, the bioadhesive properties of the polymer will be triggered so that the patch adheres to the body tissue. FIG. 5A shows a cross-sectional view of an embodiment of a medical device having a coating comprising a biocompatible polymer with triggerable bioadhesive properties whose bioadhesive properties are triggered by pressure. In this embodiment, the medical device is a balloon-expandable intravascular stent 120 having a stent sidewall structure comprising a plurality of struts 130 and a plurality of openings. A coating 50, comprising a therapeutic agent 90 and a biocompatible polymer 20 having bioadhesive functionalities 30 is disposed on the surface 60 of the struts 130 of the stent 120. If the stent has a stent sidewall structure comprising a plurality of struts and a plurality of openings, it is preferable that the coating conforms to the stent sidewall structure to preserve the openings. In FIG. 5A, the stent 120 is disposed on a delivery catheter 140 for delivery to an occlusion 210, such as a restenotic region, in a blood vessel 200. The delivery catheter 140 can include a balloon for expanding the stent 120.

Figure 5B:
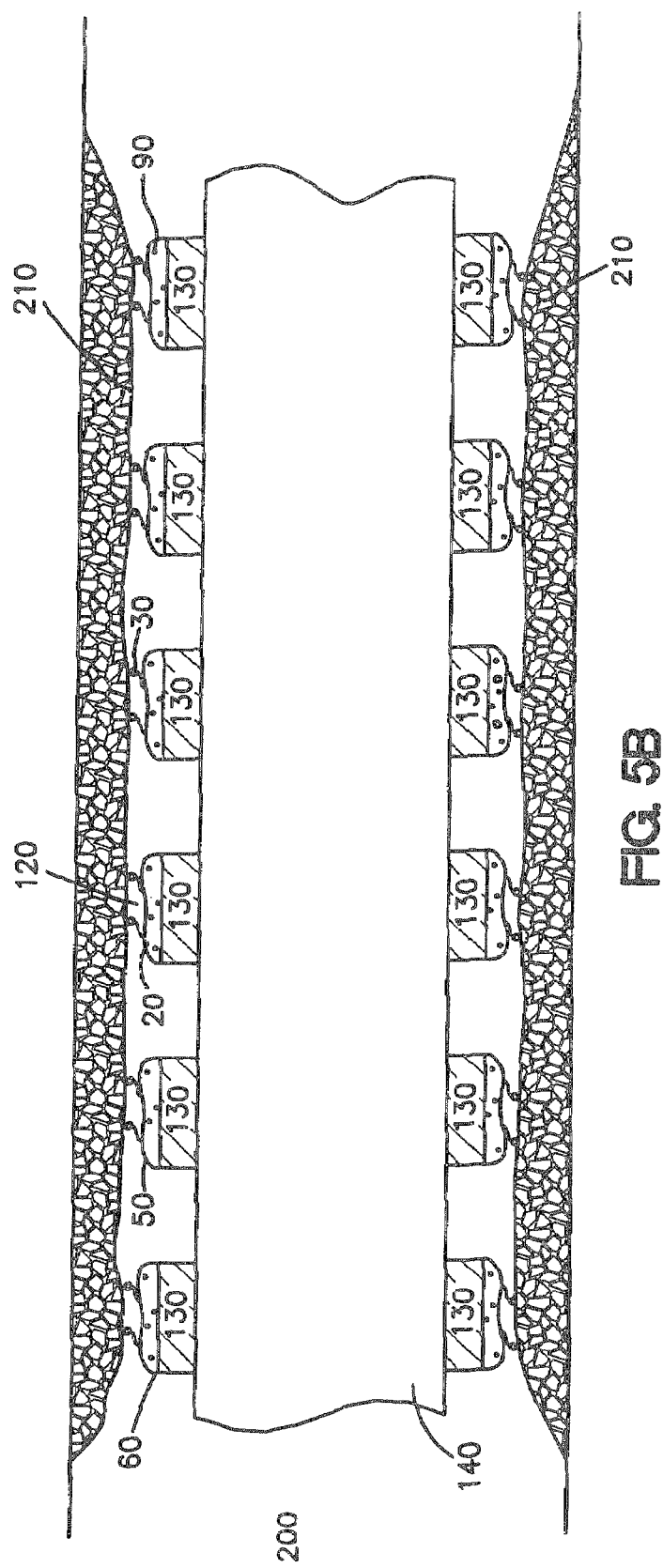
FIG. 5B shows the intravascular stent of FIG. 5A expanded and the bioadhesive properties activated.

FIG. 5B shows the delivery catheter 140 expanded to deliver the stent 120. As the delivery catheter 140 pushes against the stent 120 and asserts pressure against the pressure-sensitive polymer 20, the bioadhesive functionalities 30 are activated and the bioadhesive properties of the polymer 20 are triggered. The stent 120 can then adhere to the wall of the blood vessel 200.

In certain embodiments, medical devices can comprise a biocompatible polymer having triggerable bioadhesive properties and triggerable drug releasing properties and a therapeutic agent, wherein the bioadhesive properties and the drug release properties are controlled by a different stimulus. The ability to trigger the triggerable bioadhesive properties and the drug release properties at different times allows for control over both the degree of bioadhesion as well as the delivery rate of the therapeutic agent.

In a preferred embodiment, a medical device, such as a patch, comprises a biocompatible polymer that has a first polymer that has triggerable bioadhesive properties and a second polymer that has triggerable drug release properties. Polymers with triggerable drug release properties can have functionalities similar to bioadhesive functionalities such as functional groups bonded or embedded within a polymer. When inactive, drug release functionalities are capable of trapping a therapeutic agent and when such functionalities are activated the therapeutic agent is released from the polymer. In one embodiment, the triggerable bioadhesive properties can be triggered by applying an electric potential to the first polymer. The triggerable drug release properties of the biocompatible polymer can be triggered by exposing the second polymer of the biocompatible polymer to a change in pH. Therefore, in one example, once implanted in a body lumen the bioadhesive properties of a medical device, such as a patch, comprising a biocompatible polymer can be activated by the application of an electric potential. Then simultaneously or independently, the drug release properties can be activated by exposing the medical device to a change in pH which, in some cases, results from the medical device being implanted near an area that has an acidic environment.

Furthermore, the different triggerable properties, i.e., bioadhesive properties and drug release properties can be found within one biocompatible polymer or individual polymers each with different triggerable properties which can be combined, as described above.

In addition to controlling or manipulating bioadhesion and drug delivery rate, properties such as shape, degradation, pore size, conductivity and rheology can also be controlled and manipulated.

Stimuli

Triggerable bioadhesive properties of polymers suitable for use in the embodiments described herein can be triggered or activated upon exposure to a stimulus. Upon exposure to a stimulus the bioadhesive properties are triggered and the medical device that includes a polymer that comprises bioadhesive functionalities will adhere to body tissue. In some embodiments, the polymer will continue to adhere to the body tissue even though the medical device is no longer exposed to the stimulus. In other embodiments, the polymer will no longer be bioadhesive once the stimulus is removed. Also, in some embodiments, upon exposure to another stimulus, the bioadhesive properties can be deactivated so that the polymer becomes non-bioadhesive.

The stimulus that triggers the triggerable bioadhesive material can be generated by a source that is external or internal to the patient once the medical device has been implanted. The necessary stimulus will depend on the type of bioadhesive polymer that is used and also the type of bioadhesive properties being triggered or activated. Examples of stimuli that are suitable for the embodiments described herein include, but are not limited to, exposure to an electrical potential, exposure to a magnetic field, exposure to a change in pH, exposure to a change in temperature, exposure to pressure, exposure to an aqueous medium, exposure to light such as UV light or a combination of any of the forgoing.

Various types of devices can be used to introduce the desired stimuli. For example, a syringe or catheter can be used to deliver a solution of a desired pH in order to expose the medical device to a change in pH. Catheters equipped with a heating element can be used to change the temperature. Examples of other devices include MRI equipment for introducing such stimuli such as oscillating magnetic fields, ultrasonic equipment, and iontophoresis equipment can be used to expose the medical devices described herein to electrical potentials.

Figure 6A:
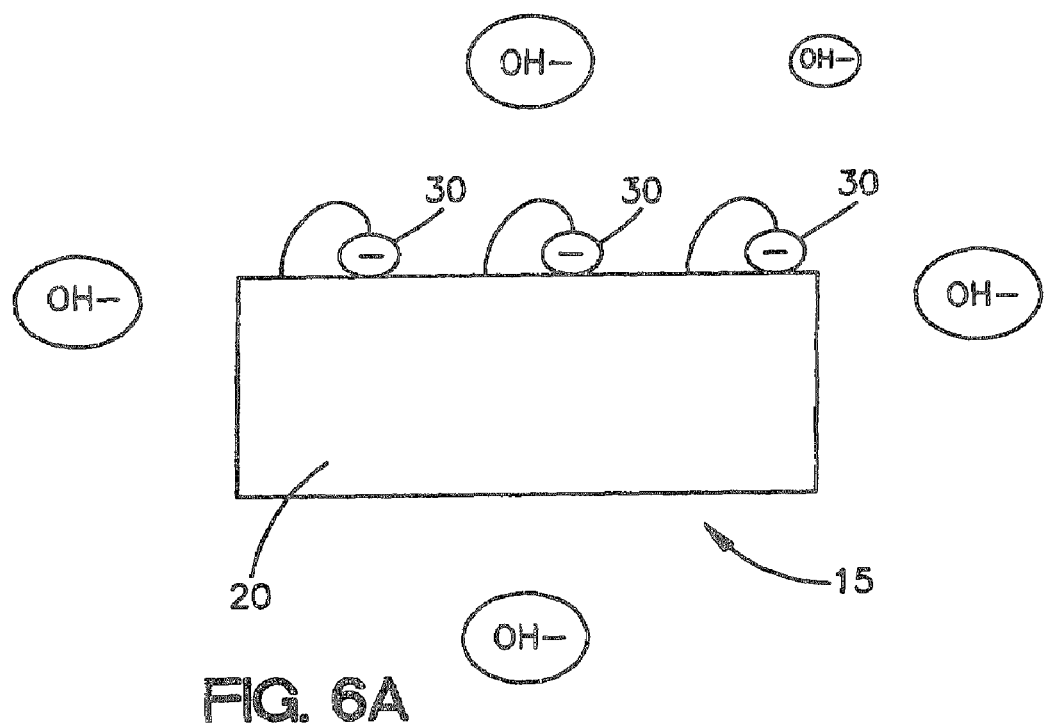
FIG. 6A shows a patch that includes a polymer with bioadhesive properties wherein the bioadhesive properties are inactive when the polymer is exposed to basic conditions.
Figure 6B:
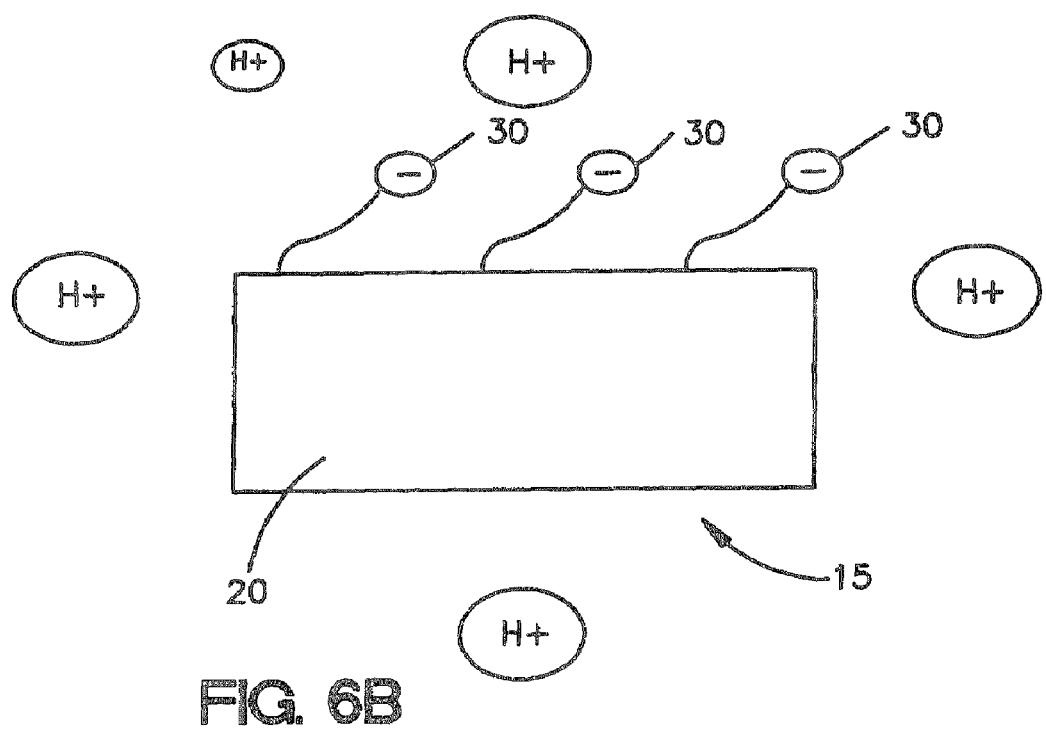
FIG. 6B shows the patch of FIG. 6A wherein the bioadhesive properties are activated when the polymer is exposed to acidic conditions.

Triggerable bioadhesive properties that can be triggered by a change in pH can be triggered by exposure to acidic tumors and infection sites. An example of the stimulus being a change in pH is shown in FIG. 6A and FIG. 6B. FIG. 6A shows a patch 15 wherein the patch 15 comprises a biocompatible polymer 20 with triggerable functionalities 30 wherein the triggerable functionalities 30 are inactive in basic conditions. FIG. 6B shows a patch 15 wherein the patch 15 comprises a biocompatible polymer 20 having triggerable functionalities 30, wherein the triggerable functionalities 30 are activated in acidic conditions.

Figure 7A:
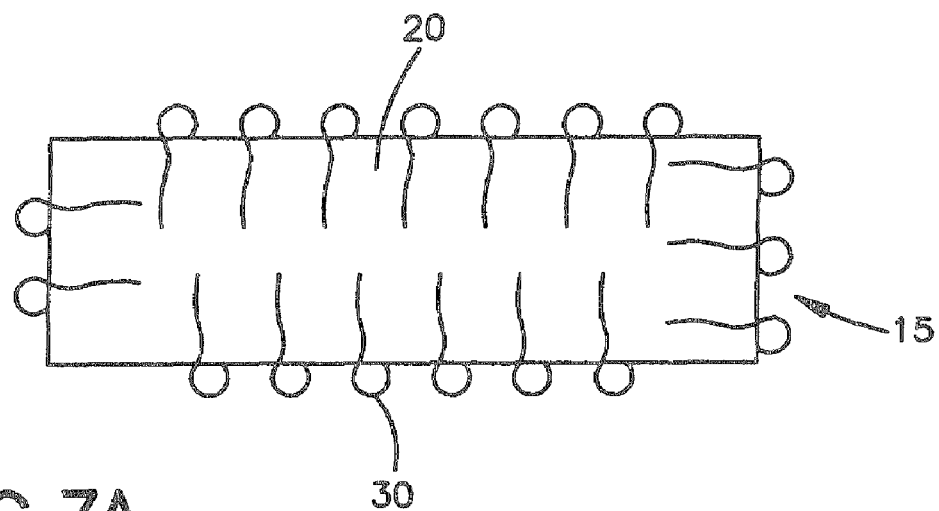
FIG. 7A shows a patch that includes a polymer with bioadhesive properties wherein the bioadhesive properties are inactive when the polymer is exposed to a non-aqueous environment.
Figure 7B:
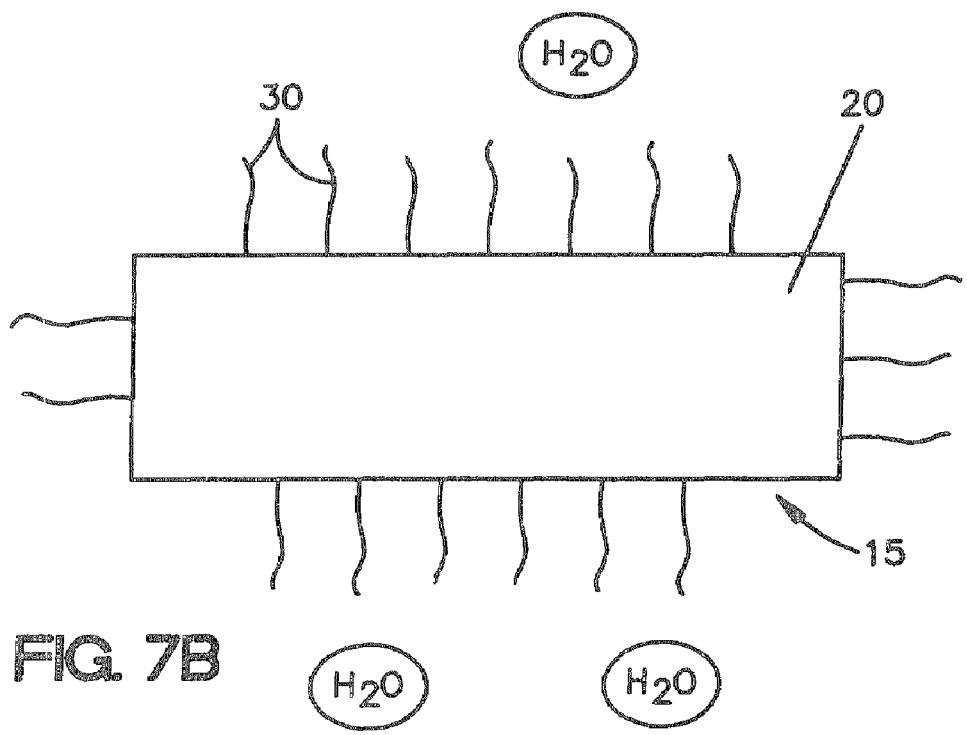
FIG. 7B shows the patch of 7A wherein the bioadhesive properties are activated when the polymer is exposed to an aqueous environment.

Additionally, triggerable bioadhesive properties that can be triggered by exposure to an aqueous environment need only be inserted into the body. An example where the stimulus is exposure to an aqueous medium is shown in FIG. 7A and FIG. 7B. FIG. 7A shows a patch 15 which comprises a biocompatible polymer 20 having bioadhesive functionalities 30 where the bioadhesive functionalities 30 are deactivated. The deactivation is caused by the triggerable functionalities being folded tightly back in on themselves within the base polymer and being unable to move in a non-aqueous medium, essentially being "trapped." FIG. 7B shows a patch 15 which comprises a biocompatible polymer 20 having bioadhesive functionalities 30 where the bioadhesive functionalities 30 are activated after being exposed to an aqueous medium. When the triggerable bioadhesive functionalities are exposed to an aqueous medium the triggerable functionalities are then free to move.

Adhesion can be measured by methods known to one skilled in the art. Suitable methods include but are not limited to the use of, microbalances, magnetic force microscopy, centrifugation, direct force measurements, atomic force microscopy, rolling ball tack tests, surface tension tests, probe tack tests, peel adhesion tests and magnetic force transducer techniques. For example, a microbalance uses a modified contact angle analyzer to perform microforce measurements using a small probe for measuring fracture strength (mN/sq.cm), deformation to failure and work of adhesion. One type of magnetic force transducer technique equipment is a CAHN machine or an EMFT machine, which provides quantitative tensile information. These are both sensitive electrobalances that measure a current through an electromagnet.

Triggerable Bioadhesive Polymers

Suitable polymers having a triggerable bioadhesive properties that can be used in the medical devices of the embodiments described herein include, but are not limited to, acid polymers such as polymers containing methacrylic acid and/or acrylic acid, styrene-isobutylene-copolymers, polyurethane and its copolymers, silicone and its copolymers (e.g., polysiloxanes and substituted polysiloxanes), ethylene-alphaolefin copolymers, acrylic polymers and copolymers, polymethacrylates, polyacrylimides, vinyl halide polymers, polyvinylidene halides, polyvinyl ethers, polyvinylidene halides, polyvinyl ketones, polyvinyl aromatics, copolymers of vinyl monomers, copolymers of vinyl monomers and olefins such as ethylene-methyl methacrylate copolymers, polyamides, alkyd resins, polycarbonates, polyoxymethylenes, ethylene-vinyl acetate copolymers, polyamides, polyimides, polyethers, epoxy resins, alkyd resins, polyurethanes, thermoplastic elastomers, polyolefins, cellulosics, polyamides, polyesters, polysulfones, polytetrafluorethylenes, fluorosilicones, polycarbonates, acrylonitrile-styrene copolymers, ABS (acrylonitrile-butadiene-styrene) resins, acrylonitrile butadiene styrene copolymers, acrylics, polylactic acid, polylactic acid-polyethylene oxide copolymers, polycarbonates, polysaccharides, phospholipids, gelatins, cellulose ethers, collagens, chitosans, and chitins, or a combination of the foregoing. Preferably, polymers include acid polymers such as methacrylic and/or acrylic acid polymers, gelatins, carboxy-methyl celluloses, hyaluronic acid polymers and pectin.

In certain applications, it may be preferable that the polymer having a triggerable bioadhesive property be a hydrogel. Examples of suitable hydrogels include cationic, anionic and chitosan based hydrogels. Suitable cationic hydrogels include networks made up of cationic monomers containing macro-monomers cross-linked within a hydrophilic network. A hydrogel suitable for the embodiments described herein can comprise a macro-monomer having a mixture of hydrophilic and hydrophobic cationic ammonium monomers, allyl methacrylate and hydrophilic monomers, for example N, N dimethyl acrylamide. In one embodiment, the macro-monomer can have between about 1% and about 20% by weight of a hydrophilic and hydrophobic cationic ammonium monomer mixture, between about 0.5% and about 5% of allyl methacrylate and the remainder of the composition can be comprised of hydrophilic monomers. Hydrophilic cationic ammonium monomers include, but are not limited to, trimethylammoniumpropyl methacylate, triethylammoniummethyl methacrylate and N-trimethylammoniumpropyl acrylamide. Hydrophobic cationic ammonium monomers include but are not limited to, alkyldimethylammoniumpropyl methacrylate, alkyldimethylammoniumethyl methacrylate and N-alkyldimethylammoniumpropyl acrylamide, wherein the alkyl group is octyl to octadecyl.

Figure 8:
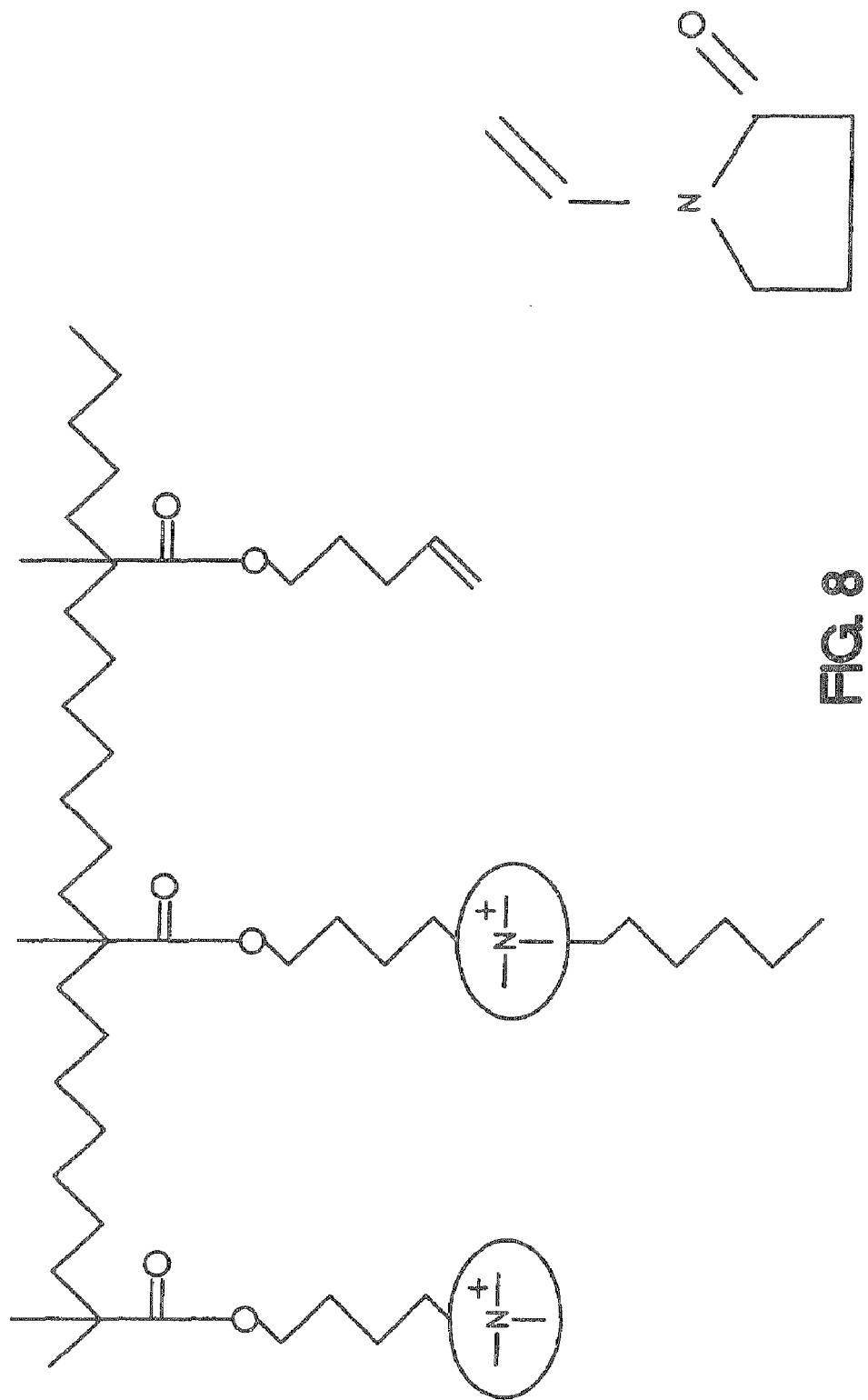
FIG. 8 shows a cationic hydrogel that can be used with the embodiments described herein.

Polymerization of the macro-monomer with a hydrophilic monomer, such as N-vinylpyrrolidone, will result in a hydrophilic cationic hydrogel. FIG. 8 shows an example of a macro-monomer that can be polymerized with N-vinylpyrrolidone to form a hydrophilic cationic hydrogel. The portions of the macro-monomer that include a cation serve as bioadhesive functionalities of the polymer having triggerable bioadhesive properties. In this example, the bioadhesive property is part of the polymer. In other embodiments, the bioadhesive property can be part of a material, such as a polymer, that is embedded in another polymer.

Polymers having a triggerable bioadhesive properties can comprise an anionic hydrogel. Suitable anionic hydrogels include networks made up of anionic monomers containing macro-monomers cross-linked within a hydrophilic network. For example, a hydrogel suitable for the embodiments described herein can be a macro-monomer containing a methacrylic acid monomer, allyl methacrylate and a hydrophilic monomer such as N,N-dimethylacrylamide. The methacrylic acid content in the macro-monomer can comprise between about 5% and about 99.5% by weight of the macro-monomer. The allyl methacrylate can comprise between about 0.5% and about 5% by weight of the macro-monomer, and the remainder of the composition can be comprised of the hydrophilic monomer.

Figure 9:
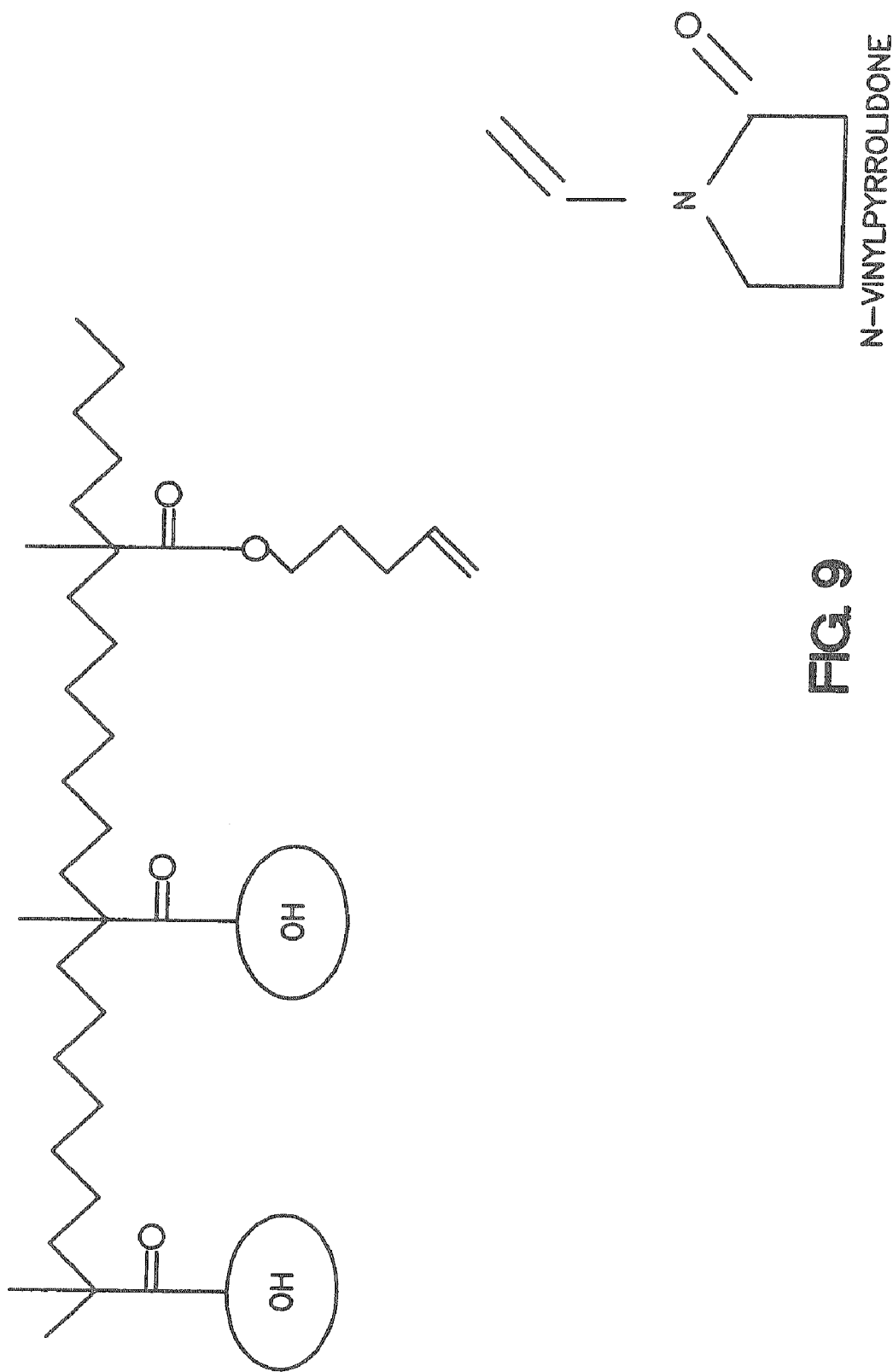
FIG. 9 shows an anionic hydrogel that can be used with the embodiments described herein.

Polymerization of the macro-monomer with a hydrophilic monomer, such as N-vinylpyrrolidone, will result in a hydrophilic anionic hydrogel. FIG. 9 shows an example of a macro-monomer that can be polymerized with N-vinylpyrrolidone to form a hydrophilic anionic hydrogel. The portions of the macro-monomer that are anionic serve as bioadhesive functionalities of the polymer.

Figure 10:
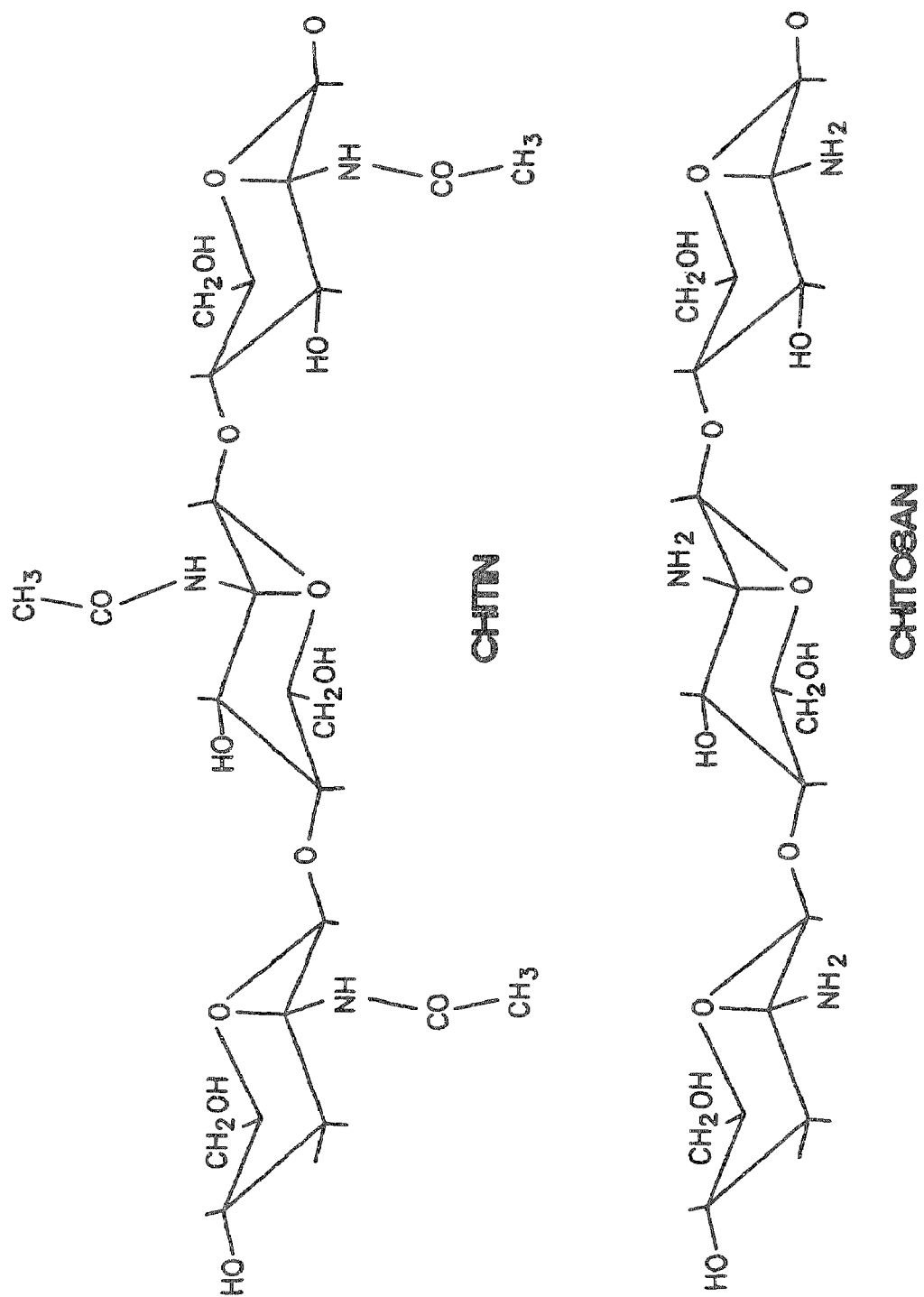
FIG. 10 shows a hydrogel that can be used with the embodiments described herein.

Another example of a suitable hydrogel is a chitosan hydrogel. Chitosan can be cross-linked into a hydrogel by reacting it with a di-epoxy molecule. For example, ethylene glycol di-glycidyl ether can be used to cross-link chitosan by heating an aqueous solution of the chitosan and di-glycidyl ether at 50-100° C. FIG. 10 shows chitosan suitable for use with the embodiments described herein and chitin.

Other suitable polymers include hyper-branched polymers such as dendrimers that have tree-like or generational architecture. Because of the way that dendrimers are formed, it is possible to make dendrimers that have various bioadhesive functionalities among the generations. For example, the ends and each generation of a dendrimer can be either hydrophilic or hydrophobic. Since each dendrimer molecule ends in a large number of functional groups, a relatively high bioadhesive force can be achieved. In the case of polyamino dendrimers, the surface of all full generations consists of multiple amines and the surface of the half generations consists of multiple acids. These two kinds of surfaces provide the means of attachment of multiple different functional components to the dendrimer, allowing the dendrimer to have desired bioadhesive properties. Also, the dendrimer can have a longer linking group at the last generation which allows the functional group at the end of the linking group to either bury itself or be available at the surface of the medical device.

The amount of polymer having a triggerable bioadhesive properties used in the medical devices of the embodiments described herein can vary depending on the application of the medical device. In some embodiments where the polymer is used to form the medical device, it is preferred that the amount of polymer used ranges from about 10% to about 100%, 30% to about 100%, 50% to about 100% or about 90% to about 100% weight percent of the medical device. More preferably, the amount of polymer used to form the medical device ranges from about 95% to about 100% weight percent of the medical device. In embodiments where the polymer is used to form a coating disposed on the medical device, it is preferred that the amount of polymer used ranges from about 0.1% to about 95% weight percent of the coating. More preferably, the amount of polymer used to form the coating ranges from about 50% to about 95% weight percent of the coating. Also, when the polymer is disposed on a medical device as a coating the polymer can be disposed on a portion or the entire medical device. For example, in certain embodiments the polymer can be disposed on the abluminal portion of a medical device, such as a stent.

Medical Devices

Types of Medical Devices

Medical devices of the embodiments described herein can be inserted into and/or implanted in the body of a patient. Medical devices that are suitable for the embodiments described herein include, but are not limited to films; gels; patches, such as endo-surgical patches; stents; surgical staples; catheters, such as central venous catheters and arterial catheters; guidewires; aneurysm coils; cannulas; cardiac pacemaker leads or lead tips; cardiac defibrillator leads or lead tips; implantable vascular access ports; blood storage bags; blood tubing; vascular or other grafts; intra-aortic balloon pumps; heart valves; cardiovascular sutures; total artificial hearts and ventricular assist pumps; and extra-corporeal devices such as blood oxygenators, blood filters, hemodialysis units, hemoperfusion units and plasmapheresis units. Additional medical devices include textiles and porous structures for use when tissue in-growth is required and nano-porous structures used for molecular transport. One preferred medical device of the embodiments described herein is a patch, film or gel.

Medical devices suitable for the embodiments described herein can have at least one surface. Additionally, medical devices suitable for the embodiments described herein can have an outer surface, an inner surface, and at least one side surface between the outer surface and the inner surface. The surfaces can also be smooth or textured. For example, a medical device suitable for the embodiments described herein can have a textured surface wherein the surface is nano-textured. A nano-textured surface is a surface that is three-dimensional comprised of nano-sized components, such as nano-bumps. Any one of the surfaces of the medical device, can be solid or have a plurality of openings therein.

Also medical devices suitable for the embodiments described herein include those that have a tubular or cylindrical-like portion. The tubular portion of the medical device need not be completely cylindrical. For instance, the cross-section of the tubular portion can be any shape, such as a circle, rectangle, or triangle. Such devices include, without limitation, stents and grafts. A bifurcated stent is also included among the medical devices which can be fabricated by the method of the embodiments described herein. In one embodiment, the medical device is a stent having a sidewall comprising a plurality of struts defining a plurality of openings. In some embodiments, the stent has an open lattice sidewall stent structure made up of openings and struts. The medical device has an outer surface that is adapted for exposure to a body lumen, an inner surface, and at least one side surface between the outer surface and the inner surface.

In addition, the tubular portion of the medical device may be a sidewall that may comprise a plurality of struts defining a plurality of openings. The sidewall defines a lumen. Also, the struts may be arranged in any suitable configuration. Also, the struts do not all have to have the same shape or geometric configuration. When the medical device is a stent comprising a plurality of struts, the surface is located on the struts. Each individual strut has an outer surface adapted for exposure to the body tissue of the patient, an inner surface, and at least one side surface between the outer surface and the inner surface.

Medical devices which are particularly suitable for the embodiments described herein include any kind of stent for medical purposes which are known to the skilled artisan. Suitable stents include, for example, vascular stents such as self-expanding stents and balloon expandable stents. Examples of self-expanding stents useful in the embodiments described herein are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

Polymers for Device Formation

Polymers that can be used to make the medical devices of the embodiments described herein include without limitation styrene-isobutylene-styrene, polystyrene, polyacrylonitrile, rayon-triacetate, Nylon 66, ethylene vinyl-acetate, polyethylene terephtalate, polyvinyl acetate, polyvinyl chloride, polyvinyl methyl ether, polyvinylidene fluoride, polyvinylidene chloride, polyglycolic acid, polycaprolactone, cellulose, cellulose acetate, cellulose butyrate, cellulose acetate butyrate, cellophane, cellulose nitrate, cellulose propionate, carboxymethyl cellulose, polylactic acid, polyglycolic acid, polyethylene glycol or a combination of the foregoing. For medical devices which undergo mechanical challenges, e.g., expansion and contraction, the polymers can be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Other polymers which can be used include ones that can be dissolved and cured or polymerized on the medical device or polymers having relatively low melting points that can be blended with biologically active materials.

Metallic Materials for Device Formation

In certain embodiments, where the biocompatible polymer with triggerable bioadhesive properties are used as a coating disposed on a medical device, the medical device can be metallic. Suitable metallic materials useful for making the substrate include, but are not limited to, metals and alloys based on titanium (such as nitinol, nickel titanium alloys, thermo memory alloy materials), stainless steel, gold, platinum, iridium, molybdenum, niobium, palladium, chromium, tantalum, nickel chrome, or certain cobalt alloys including cobalt chromium nickel alloys such as Elgiloy® and Phynox®, or a combination thereof. Other metallic materials that can be used to make the medical device include clad composite filaments, such as those disclosed in WO 94/16646.

In certain embodiments, the substrate comprises a metal oxide. Suitable metal oxides include, but are not limited to, transition metal oxides, platinum oxide, tantalum oxide, titanium oxide, titanium dioxide, iridium oxide, niobium oxide, zirconium oxide, tungsten oxide, rhodium oxide, or a combination thereof. Preferably, the metal or metal oxide is biocompatible.

Preferably, the metal or metal oxide region comprises a radiopaque material. Including a radiopaque material may be desired so that the medical device is visible under X-ray or fluoroscopy. Suitable materials that are radiopaque include, but are not limited to, gold, tantalum, platinum, bismuth, iridium, zirconium, iodine, barium, silver, tin, alloys of these metals, or a combination thereof.

Furthermore, although certain embodiments can be practiced by using a single type of metal to form the substrate, various combinations of metals can also be employed. The appropriate mixture of metals can be coordinated to produce desired effects when incorporated into a substrate.

Ceramic Materials for Device Formation

In certain embodiments, where the biocompatible polymer with triggerable bioadhesive properties are used as a coating disposed on a medical device, the medical device can be made of a ceramic material. Suitable ceramic materials used for making the substrate include, but are not limited to, oxides, carbides, or nitrides of the transition elements such as titanium oxides, hafnium oxides, iridium oxides, chromium oxides, aluminum oxides, zirconium oxides, or a combination thereof. Silicon based materials, such as silica, may also be used.

Furthermore, although certain embodiments can be practiced by using a single type of ceramic to form the substrate, various combinations of ceramics can also be employed. The appropriate mixture of ceramics can be coordinated to produce desired effects when incorporated into a substrate.

Therapeutic Agents

The term "therapeutic agent" as used herein encompasses drugs, genetic materials, and biological materials and can be used interchangeably with "biologically active material." The term "genetic materials" means DNA or RNA, including, without limitation, DNA/RNA encoding a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g. IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other suitable therapeutic agents include:
- anti-thrombogenic agents such as heparin, heparin derivatives, urokinase, and PPack (dextrophenylalanine proline arginine chloromethylketone);
- anti-proliferative agents such as enoxaprin, angiopeptin, or monoclonal antibodies capable of blocking smooth muscle cell proliferation, hirudin, acetylsalicylic acid, tacrolimus, everolimus, pimecrolimus, sirolimus, zotarolimus, amlodipine and doxazosin;
- anti-inflammatory agents such as glucocorticoids, betamethasone, dexamethasone, prednisolone, corticosterone, budesonide, estrogen, sulfasalazine, rosiglitazone, mycophenolic acid and mesalamine;
- anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives, paclitaxel as well as its derivatives, analogs or paclitaxel bound to proteins, e.g. Abraxane™;
- anesthetic agents such as lidocaine, bupivacaine, and ropivacaine;
- anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;
- DNA demethylating drugs such as 5-azacytidine, which is also categorized as a RNA or DNA metabolite that inhibit cell growth and induce apoptosis in certain cancer cells;
- vascular cell growth promoters such as growth factors, vascular endothelial growth factors (VEGF, all types including VEGF-2), growth factor receptors, transcriptional activators, and translational promoters;
- vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;
- a cholesterol-lowering agents, vasodilating agents, and agents which interfere with endogenous vasoactive mechanisms;
- anti-oxidants, such as probucol;
- antibiotic agents, such as penicillin, cefoxitin, oxacillin, tobranycin, daunomycin, mitocycin;
- angiogenic substances, such as acidic and basic fibroblast growth factors, estrogen including estradiol (E2), estriol (E3) and 17-beta estradiol;
- drugs for heart failure, such as digoxin, beta-blockers, angiotensin-converting enzyme (ACE) inhibitors including captopril and enalopril, statins and related compounds;
- macrolides such as sirolimus (rapamycin) or everolimus; and
- AGE-breakers including alagebrium chloride (ALT-711).

Other therapeutic agents include nitroglycerin, nitrous oxides, nitric oxides, antibiotics, aspirins, digitalis, estrogen, estradiol and glycosides. Preferred therapeutic agents include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogs, or paclitaxel derivatives, and mixtures thereof). For example, derivatives suitable for use in the embodiments described herein include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other preferred therapeutic agents include tacrolimus; halofuginone; inhibitors of HSP90 heat shock proteins such as geldanamycin; microtubule stabilizing agents such as epothilone D; phosphodiesterase inhibitors such as cliostazole; Barkct inhibitors; phospholamban inhibitors; and Serca 2 gene/proteins. In yet another preferred embodiment, the therapeutic agent is an antibiotic such as erythromycin, amphotericin, rapamycin, adriamycin, etc.

In preferred embodiments, the therapeutic agent comprises daunomycin, mitocycin, dexamethasone, everolimus, tacrolimus, zotarolimus, heparin, aspirin, warfarin, ticlopidine, salsalate, diflunisal, ibuprofen, ketoprofen, nabumetone, prioxicam, naproxen, diclofenac, indomethacin, sulindac, tolmetin, etodolac, ketorolac, oxaprozin, celcoxib, alagebrium chloride or a combination thereof.

The therapeutic agents can be synthesized by methods well known to one skilled in the art. Alternatively, the therapeutic agents can be purchased from chemical and pharmaceutical companies.

The amount of therapeutic agent present in the medical device or the coating for the medical device can be adjusted to meet the needs of the patient. In general, the amount of the therapeutic agent used may vary depending on the application or therapeutic agent selected. In addition, the quantity of the therapeutic agent used may be related to the selection of the polymer. In certain embodiments, the therapeutic agent comprises at least 5%, at least 10%, at least 20%, at least 30%, at least 40%, at least 50%, at least 60%, at least 70%, at least 80%, at least 90%, at least 95%, at least 97%, at least 99% or more by weight of the polymer having a triggerable bioadhesive property. In certain embodiments, the therapeutic agent comprises between about 0.01% and about 5% by weight of the polymer having a triggerable bioadhesive property.

Additionally, the medical devices described herein can further comprise more than one therapeutic agent. In one embodiment the medical device can have a first and second therapeutic agent wherein the first therapeutic agent can assist in the healing of a lesion. Such therapeutic agents can include statins, like simvastatin, fluvastatin, rosuvastatin; endothelin receptor antagonists, such as bosentan; collagen synthesis inhibitors, such as tranilast; adenosine receptor agonists, such as HE-NECA, prostaglandin E agonists, such as alprostadil (PGE1); adenosine A2 receptor agonists, such as CGS21680, or peroxisome proliferators such as fenofibrate. The second therapeutic agent can be an anti-proliferation drug, to prevent the development of smooth muscle cells, such as paclitaxel. Additionally the second therapeutic agent can be an endothelial growth factor to encourage endothelialization or epithelial growth factor for mucosal tissue.

Figure 11:
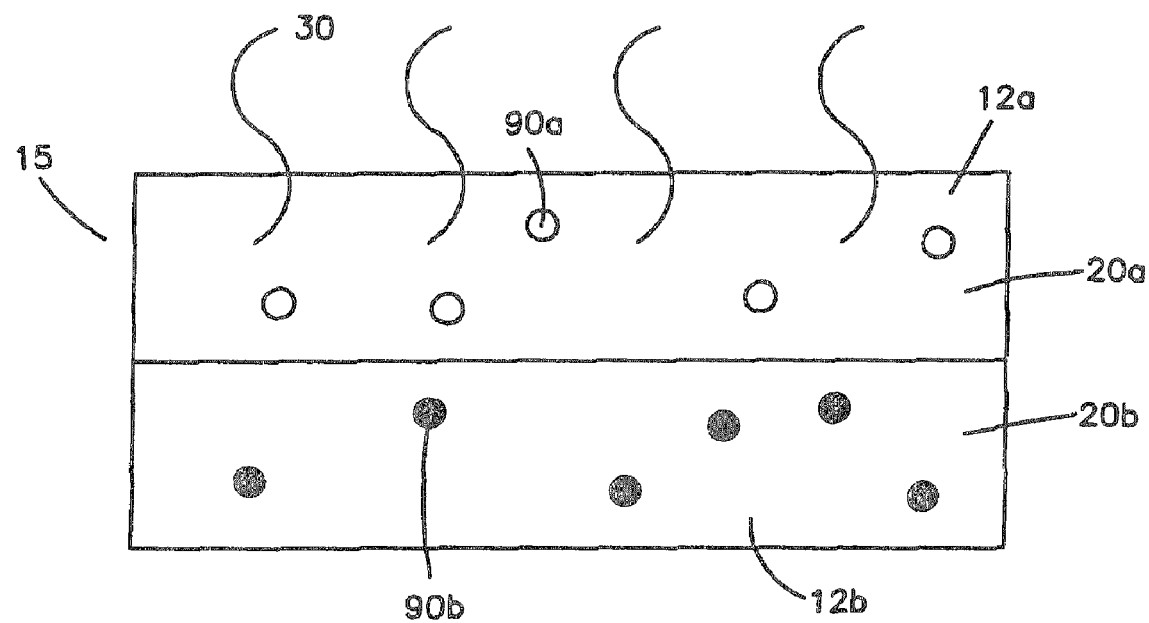
FIG. 11 shows a two-layer patch comprising a biocompatible polymer having triggerable bioadhesive properties and two therapeutic agents.

For example, FIG. 11 shows a two-layer patch 15 wherein in the top layer 12a comprises a biocompatible polymer 20a with triggerable bioadhesive functionalities 30 and a first therapeutic agent 90a and wherein the bottom layer 12b comprises a biocompatible polymer 20b, which has a second therapeutic agent 90b, and may or may not have triggerable bioadhesive properties.

In one embodiment, once the patch is implanted, the bioadhesive functionalities 30 of the polymer 20a in the top layer 12a can be activated and the patch can be applied over a region of a body lumen in need of treatment, such as an arterial lesion. Also, when the bioadhesive functionalities 30 are activated and the patch 15 adheres to the treatment site, the first therapeutic agent 90a can be released to treat the body lumen. Also, the second therapeutic agent 90b, in the bottom layer 12b can also be released simultaneously or sequentially with the first therapeutic agent.

Methods of Making

The embodiments described herein can be made by any means known in the art. One preferred method of making a medical device described herein, for example a patch, can comprise the steps of dissolving or suspending the biocompatible polymer having triggerable bioadhesive properties in a solvent; dispersing the solution or suspension; and removing the solvent. Upon removal of the solvent the biocompatible polymer having a triggerable bioadhesive properties results in a thin film of a preferred thickness. The film can then can be molded or cut to the dimensions needed.

Another preferred method of making a medical device described herein, for example a bioadhesive stent, can comprise the steps of dissolving or suspending the biocompatible polymer having a triggerable bioadhesive property in a solvent; and coating the medical device, for example a stent, with the solution or suspension.

Examples of suitable methods of applying a coating to a medical device include, but are not limited to, spraying, dipping, or direct deposition. Suitable solvents for dissolving or suspending biocompatible polymer having triggerable bioadhesive properties to form a solution can be, without limitation, tetrahydrofuran, chloroform, toluene, acetone, isooctane, 1,1,1-trichloroethane, or a mixture thereof.

Preferably, once the medical devices are made, the triggerable functionalities of the biocompatible polymer are deactivated. For example, if the triggerable functionalities of the biocompatible polymer having triggerable bioadhesive properties are deactivated in acidic medium the medical device can be washed with or dipped in acid.

The polymers described herein can be used for a variety of applications, for example such polymers can be used to allow an implantable medical device to adhere to body tissue. Other uses include, but are not limited to, treating ulcers (e.g., materials for covering and treating ulcers); treating arterial plaque (e.g., drug-filled patch to be deployed through a catheter to cover and treat arterial plaque); promoting tissue in-growth (e.g., textiles and porous structures for encouraging tissue in-growth); delivering therapeutic agents; dressing wounds; forming hempstatic films, dura mater, pericardial replacement, tissue engineered scaffolds; providing nanoporous structures that may be necessary when molecule transport is required but not cellular transport; and providing coverings for Barretts Syndrome (prophylacticly or after ablation). The polymers having a triggerable bioadhesive property can also be used with or adhere to mucosal tissue such as in the gastrointestinal tract.

One method of using the embodiments described herein include the following steps: providing an implantable medical device comprising a biocompatible polymer having triggerable bioadhesive properties and exposing the polymer to a stimulus to trigger the bioadhesive property. The triggerable bioadhesive properties allow the implantable medical device to adhere to body tissue when the polymer is exposed to a stimulus. The medical device comprising a biocompatible polymer having triggerable bioadhesive properties can further be removed from a body tissue by removing the stimulus and deactivating the bioadhesive property. Additionally, the medical device comprising a biocompatible polymer having triggerable bioadhesive properties can further be reapplied to a body tissue by again exposing the biocompatible polymer to the stimulus.

The polymers having triggerable bioadhesive properties described herein can be incorporated into different types of materials, such as medical devices, porous materials, textiles, spun materials, and non-woven materials to name a few.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

What is claimed is:

1. A medical device for implantation in the body of a patient which is an implantable patch disposed on a delivery device that is configured to supply an electrical potential, said implantable patch comprising a nanotextured surface and a coating disposed on the surface, wherein the coating comprises a therapeutic agent and a biocompatible polymer having a triggerable bioadhesive property comprising charged bioadhesive functionalities which are activated and provide the polymer with a bioadhesive property that allows the implantable medical device to adhere to body tissue when the polymer is exposed to a stimulus that comprises said electrical potential, wherein the textured surface enhances adhesion said body tissue.

2. The medical device of claim 1, wherein the polymer retains its bioadhesive property after the polymer is no longer exposed to the stimulus.

3. The medical device of claim 1, wherein the polymer is non-bioadhesive to the body tissue when the stimulus is not present.

4. The medical device of claim 1, wherein the stimulus is generated by a source that is external to the body.

5. The medical device of claim 1, wherein the stimulus is generated by a source that is internal to the body.

6. The medical device of claim 1, wherein the polymer comprises a hydrogel.

7. The medical device of claim 1, wherein the polymer comprises a cationic hydrogel comprising a macro-monomer comprising a mixture of hydrophilic and hydrophobic cationic ammonium monomers; an allyl methacrylate monomer and an N, N dimethyl acrylamide monomer.

8. The medical device of claim 1, wherein the polymer comprises a hydrogel comprising chitosan.

9. The medical device of claim 1, wherein the polymer comprises styrene-isobutylene-styrene copolymers, polyurethanes, silicones, polyesters, polyolefins, acrylic polymers and copolymers, polymethacrylates, polyacrylimides, vinyl halide polymers, polyvinyl ethers, polyvinylidene halides, polyacrylonitrile, polyvinyl ketones, polyvinyl aromatics, polyvinyl esters, copolymers of vinyl monomers, copolymers of vinyl monomers and olefins, polyamides, alkyd resins, polycarbonates, polyoxymethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, chitosans, polylactic acid, polyglycolic acid, polylactic acid-polyethylene oxide copolymers, fluorosilicones, polyethylene glycol, polysaccharides, phospholipids, or a combination of any of the foregoing.

10. The medical device of claim 1, wherein the polymer comprises polyethylene glycol, hydroxyethyl methacrylate, polyvinyl pyrrolidone, an alginate, a cross-linked gelatin or a combination of any of the foregoing.

11. The medical device of claim 1, wherein the polymer comprises a first polymer and a second polymer.

12. The medical device of claim 11, wherein the second polymer is embedded in the first polymer and wherein the second polymer is said polymer that has a triggerable bioadhesive property.

13. The medical device of claim 1, wherein the therapeutic agent comprises an anti-thrombogenic agent, anti-angiogenesis agent, anti-proliferative agent, anti-biotic agent, anti-restenosis agent, growth factor, immunosuppressant, radiochemical, or combination of thereof.

14. The medical device of claim 1, wherein the therapeutic agent comprises an anti-restenotic agent.

15. The medical device of claim 1, wherein the therapeutic agent comprises sirolimus, everolimus, tacrolimus, pimecrolimus, or zotarolimus.

16. The medical device of claim 1, wherein the therapeutic agent comprises paclitaxel.

17. An implantable patch comprising a metal or a metal alloy, said patch comprising a first surface, a second surface that is opposite the first surface, a first coating disposed on the first surface, wherein the first coating comprises a therapeutic agent and a first biocompatible polymer having a first triggerable bioadhesive property comprising positively charged bioadhesive functionalities which are activated and provide the first polymer with a bioadhesive property that allows the patch to adhere to body tissue when the first polymer is exposed to a first stimulus that comprises a first electrical potential, and a second coating disposed on the second surface, wherein the second coating comprises a second biocompatible polymer having a second triggerable bioadhesive property comprising negatively charged bioadhesive functionalities which are activated and provide the second polymer with a property that allows the patch to adhere to a surface of an additional device when the second polymer is exposed to a second stimulus that comprises a second electrical potential.

18. The patch of claim 17, wherein the second coating further comprises a therapeutic agent.

19. The medical device of claim 1, wherein said implantable medical device comprises a metal or a metal alloy.

20. The medical device of claim 1, comprising an additional device for delivering said stimulus.

21. The medical device of claim 20, wherein said additional device for delivering said stimulus is a catheter.

22. The medical device of claim 1, wherein the therapeutic agent comprises an anti-restenotic agent.

23. The medical device of claim 1, wherein said charged bioadhesive functionalities are positively charged bioadhesive functionalities.

24. The medical device of claim 22, wherein said charged bioadhesive functionalities are positively charged bioadhesive functionalities.

25. The medical device of claim 24, wherein said polymer comprises chitosan.

26. The medical device of claim 24, wherein said implantable medical device comprises a metal or a metal alloy.

27. The medical device of claim 25, wherein said implantable medical device comprises a metal or a metal alloy.

28. The medical device of claim 17, wherein said implantable patch comprises a metal or a metal alloy.

29. The medical device of claim 17, wherein the therapeutic agent comprises an anti-restenotic agent.

30. The medical device of claim 17, wherein said first polymer comprises chitosan.

31. The medical device of claim 17, wherein said implantable patch comprises a metal or a metal alloy and wherein the therapeutic agent comprises an anti-restenotic agent.

32. The medical device of claim 31, wherein said first polymer comprises chitosan.

33. The medical device of claim 1, wherein said delivery device is a catheter that is adapted to deploy said patch at a site of arterial plaque.

* * * * *